US011305010B2

(12) United States Patent
Janda

(10) Patent No.: US 11,305,010 B2
(45) Date of Patent: Apr. 19, 2022

(54) SYNTHETIC OPIOID VACCINE

(71) Applicant: THE SCRIPPS RESEARCH INSTITUTE, La Jolla, CA (US)

(72) Inventor: Kim D. Janda, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 791 days.

(21) Appl. No.: 16/071,199

(22) PCT Filed: Jan. 18, 2017

(86) PCT No.: PCT/US2017/013865
§ 371 (c)(1),
(2) Date: Jul. 19, 2018

(87) PCT Pub. No.: WO2017/127390
PCT Pub. Date: Jul. 27, 2017

(65) Prior Publication Data
US 2021/0128720 A1 May 6, 2021

Related U.S. Application Data

(60) Provisional application No. 62/281,262, filed on Jan. 21, 2016.

(51) Int. Cl.
A61K 31/385 (2006.01)
A61K 47/64 (2017.01)
A61P 25/30 (2006.01)
A61K 47/68 (2017.01)
A61K 39/00 (2006.01)
A61K 39/395 (2006.01)
A61K 39/385 (2006.01)

(52) U.S. Cl.
CPC ........ *A61K 39/385* (2013.01); *A61K 39/0013* (2013.01); *A61K 39/395* (2013.01); *A61K 47/643* (2017.08); *A61K 47/6829* (2017.08); *A61P 25/30* (2018.01)

(58) Field of Classification Search
None
See application file for complete search history.

(56) References Cited

U.S. PATENT DOCUMENTS

| 5,610,283 A | 3/1997 | Beuchler |
| 6,262,265 B1 | 7/2001 | Rouhani et al. |
| 7,109,310 B2 * | 9/2006 | McConnell .......... C07D 211/58 435/188 |
| 8,357,375 B2 | 1/2013 | Palma et al. |
| 2003/0170728 A1 * | 9/2003 | McConnell ........ G01N 33/9486 435/7.1 |
| 2011/0182918 A1 * | 7/2011 | Kalnik .................... A61P 25/36 424/175.1 |
| 2014/0377779 A1 * | 12/2014 | Yong .................... C07K 16/283 435/7.23 |
| 2015/0343054 A1 | 12/2015 | Janda |
| 2015/0374836 A1 | 12/2015 | Portoghese et al. |

FOREIGN PATENT DOCUMENTS

| CN | 02150665.5 A | 7/2003 |
| WO | 2014124317 A1 | 8/2014 |

OTHER PUBLICATIONS

Extended European Search Report dated Jul. 26, 2019 for European Patent Application No. 17741829.0.

* cited by examiner

*Primary Examiner* — Phuong Huynh
(74) *Attorney, Agent, or Firm* — Hugh Wang; Thomas Fitting

(57) ABSTRACT

Fentanyl is an addictive prescription opioid that is over 80 times mora potent than morphine. The synthetic nature of fentanyl has enabled the creation of dangerous "designer drug' analogues that escape toxicology screening, yet display comparable potency to the parent drug. Alarmingly, a large number of fatalities have been linked to overdose of fentanyl derivatives. Herein, we report an effective immunotherapy for reducing the psychoactive effects of fentanyl class drugs. A single conjugate vaccine was created that elicited high levels of antibodies with cross-reactivity for a wide panel of fentanyl analogues, Moreover, vaccinated mice gained significant protection from lethal fentanyl doses. Lastly, a surface plasmon resonance (SPR)-based technique was established enabling drug specificity profiling of antibodies derived directly from serum. Our newly developed fentanyl vaccine and analytical methods may assist in the battle against synthetic opioid abuse.

7 Claims, 4 Drawing Sheets

Fentanyl-Tetanus Toxoid Immunoconjugate (Fent-TT)

Fentanyl (Fent): $R_1$=Me
Acetylfentanyl (Ac): $R_1$=H
Butylfentanyl (Bu): $R_1$=Pr
Tolylfentanyl (Tol): $R_1$=Me, $R_2$=Me
3-Methylfentanyl (3-Me) $R_1$=Me, $R_4$=Me
α-Methylfentanyl (α-Me) $R_1$=Me, $R_4$=Me
*Unspecified R Groups = H*

SYNTHETIC OPIOID VACCINE

CROSS-REFERENCE TO RELATED APPLICATIONS

This application is a Section 371 US national phase of International Application No. PCT/US2017/013865, filed Jan. 18, 2017, which claims priority to U.S. application Ser. No. 62/281,262, filed Jan. 12, 2016, the disclosure of which is incorporated herein by reference in its entirety.

Related patent applications by the inventor herein include: U.S. Ser. No. 12/374,908, PCT07/074976, WO08/016976, "Vaccines and method for controlling adiposity"; U.S. Ser. No. 09/038,546, PCT09/038546, WO09/120954, "Nicotine conjugates"; U.S. Ser. No. 13/984,230, PCT12/000079, WO12/108960, "Ghrelin mimetic polypeptide hapten immunoconjugates having is solubility and immunogenicity and methods of use thereof"; U.S. Ser. No. 13/261,217, PCT10/002489, WO11/031327, "Nicotine haptens, immunoconjugates, and their uses"; U.S. Ser. No. 14/367,511, PCT11/001997, WO13/095321, "Heroin haptens, immunoconjugates, and related uses"; U.S. Ser. No. 14/901,794, PCT14/045019, WO15/002929, "Methods and compositions for treating obesity"; U.S. Ser. No. 14/901,799, PCT14/045023, WO15/002391, "Compositions and methods for treating obesity"; and, PCT15/031583, WO15/179403, "Enantiopure haptens for nicotine vaccine development"; the disclosures of which are incorporated herein by reference in their entireties.

STATEMENT OF GOVERNMENT SUPPORT

This invention was made with government support under grant number DA039634 awarded by the National Institutes of Health. The government has certain rights in the invention.

BACKGROUND

Fentanyl is an effective synthetic opioid that is used legally as a schedule II prescription pain reliever. However, fentanyl presents a significant abuse liability due to the euphonic feeling it induces via activation of mu-opioid receptors (MOR) in the brain; the same pharmacological target as the illegal schedule I opioid, heroin.[1] Excessive activation of MOR results in respiratory depression which can be fatal.[2] Fentanyl exceeds the potency of heroin by >10-fold, and morphine by >80-fold posing a significant risk of overdose when it is consumed from unregulated sources.[3] Furthermore, the ease of fentanyl synthesis enables illegal production and the creation of designer drug analogues.[4] The fact that the pharmacology of these analogues has yet to be properly characterized makes them particularly dangerous, especially when certain modifications, even methyl additions, can increase potency, notably at the 3-position.[5]

Last July, the National Institute on Drug Abuse (NIDA) reported an alarming surge in fentanyl overdose deaths:[6] the latest update in a long stream of overdose cases starting with methylfentanyl aka "China White" in the late 1980s.[7] A newer designer analogue, acetylfentanyl, further exacerbates the opioid epidemic because of its deceptive sale as heroin or as a heroin mixture,[8] and it has been linked to a number of overdose deaths.[9] In addition to the US, fentanyl abuse is on the rise across Europe; while the most overdose deaths occurred in Estonia, the highest consumption of fentanyl per capita was reported in Germany and Austria.[10]

SUMMARY

The invention provides, in various embodiments, a hapten for generating, when conjugated with a carrier, a vaccine for raising IgG antibodies in vivo, with specificity for fentanyl class drugs, comprising a compound of formula (I)

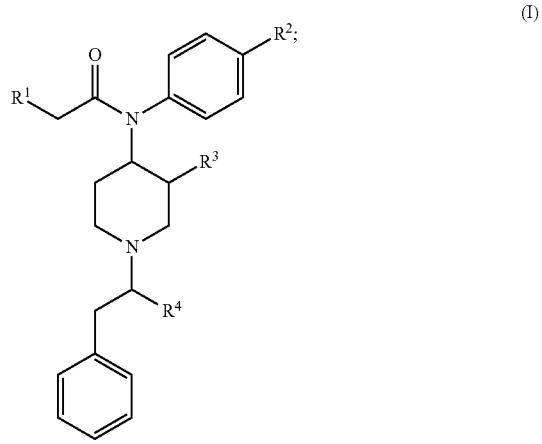

wherein $R^1=CH_2CH_2C(=O)X$ and $X=OH$ or an activated ester thereof; $R^2=H$ or a $(C_1-C_4)$alkyl group, $R^3=H$ or a $(C_1-C_4)$alkyl group, and $R^4=H$ or a $(C_1-C_4)$alkyl group; and a hapten conjugate for generating an in vivo 'immunoantagonist' to a fentanyl class drug, comprising a compound of formula (I) of claim 1 wherein X comprises a protein carrier or an amino-functionalized bead, the protein or the bead forming an amide bond with the hapten. For example, the protein carrier can be bovine serum albumin (BSA) or tetanus toxoid (TT), or the amino-functionalized bead can be a DYNABEADS® M-270 Amine.

The invention further provides a vaccine produced in a mammal by administration of an effective dose of the hapten conjugate described above. For example, the mammal used for vaccine production can be a mouse. The vaccine can comprise IgG type antibodies.

In additional embodiments, the invention provides a method of effectively minimizing a concentration of a fentanyl class drug at a site of action in a patient, comprising administration of an effective dose of the vaccine to the patient. Additionally, administration of the effective dose of the vaccine imparts significant protection to the patient from an otherwise lethal dose of a fentanyl class drug. Further, administration of the effective dose of the vaccine to the patient reduces the addiction liability and overdose potential of the fentanyl class drug.

BRIEF DESCRIPTION OF THE FIGURES

FIG. 1, Structures of fentanyl immunoconjugate and analogues recognized by polyclonal antibodies with <100 nM affinity.

FIG. 2. Timeline of experiments and anti-fentanyl antibody titers, Fent-TT (50 µg) was formulated with alum (750 µg) CpG GDN 1826 (50 µg) and administered i.p. to each mouse (N=6). IgG titers were determined by ELISA against fentanyl-BSA conjugate. Points denote means±SEM. Key: i=vaccine injection, a=antinociception assay, f=affinity determination by SPR b=blood/brain biodistribution study.

DETAILED DESCRIPTION

Figure 3:
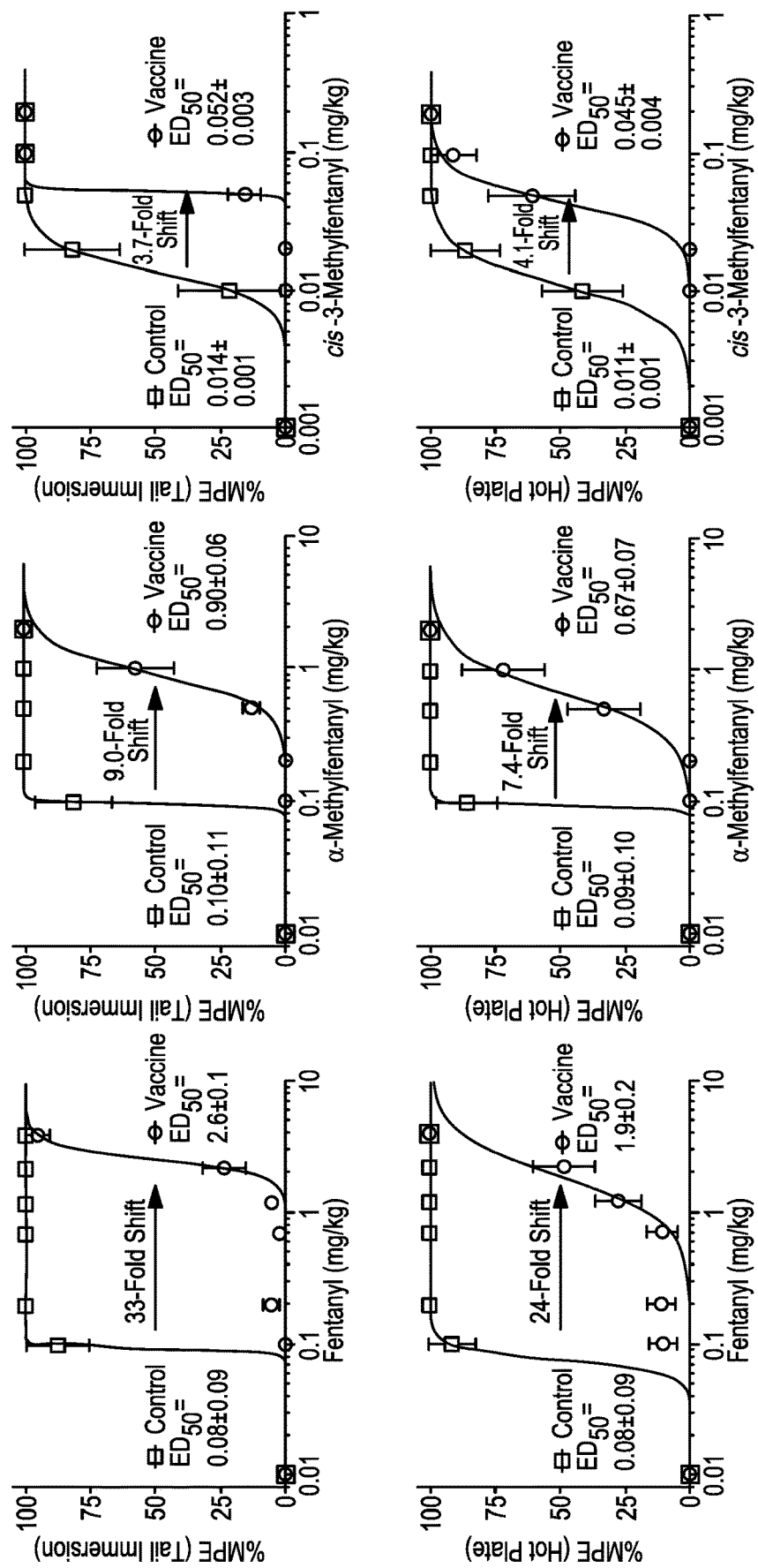
FIG. 3. Fentanyl analogue dose-response curves and $ED_{50}$ values in antinociception assays. Vaccinated and control mice (N=6 each) were cumulatively dosed with the specified drug and latency to nociception was measured by tail immersion (top) and hot plate (bottom) tests. Points denote means±SEM. For all three drugs, p-values were <0.001 in comparing control vs. vaccine groups by an unpaired t test.
Figure 4:
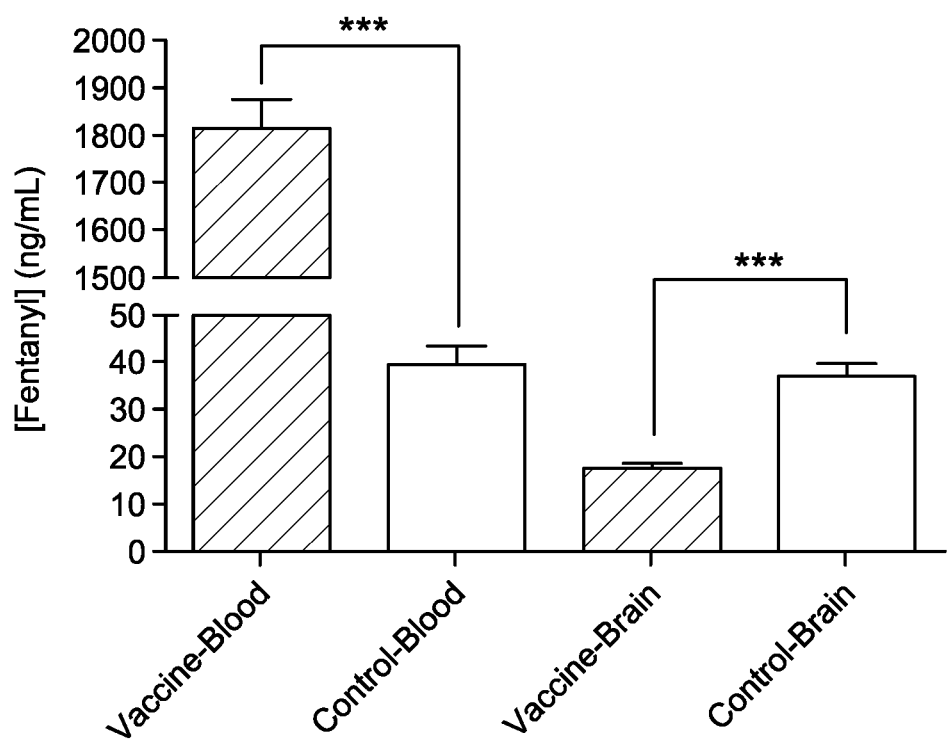
FIG. 4. Biodistribution of fentanyl in blood and brain samples. Vaccinated and control mice (N=6 each) were dosed with 0.2 mg/kg fentanyl and tissue was harvested 15 min post-injection. Fentanyl quantification was performed by LCMS analysis. Bars denote means+SEM. *** p<0.001, unpaired t test.

To combat the harmful and addictive effects of fentanyl and its analogues, we pursued an immunopharmacotherapeutic approach, similar to previous campaigns for addiction therapeutics against cocaine,[11] nicotine,[12] methamphetamine[13] and heroin,[14] The basis of this strategy involves active vaccination of a protein-drug conjugate to generate an in vivo 'immunoantagonist', which effectively minimizes concentrations of the target drug at the sites of action. As a result, the vaccine reduces the addiction liability and overdose potential of the specific drug. In this work, we report the first instance of an efficacious fentanyl conjugate vaccine. Upon immunization, this vaccine successfully stimulated endogenous generation of IgG antibodies with specificity for fentanyl class drugs. Moreover, mouse antiserum showed nanomolar affinity for a variety of fentanyl analogues by SPR-analytical methods. When mice were dosed with potentially lethal quantities of fentanyl analogues, the vaccine imparted significant protection, No other vaccines to date have demonstrated blockade of the acutely lethal effects of any drugs of abuse, Importantly, our research efforts have yielded significant progress for mitigating the pharmacodynamic effects of fentanyl class drugs.

In developing a fentanyl vaccine, hapten design presented the initial and possibly the most crucial challenge. As we have reported previously, smell/molecule haptens must faithfully preserve the natural structure of the target molecule to make a successful immunoconjugate.[15]

Confronted not only with fentanyl, but also designer analogues, our hapten incorporated the core N-(1-phenethylpiperidin-4-yl)-N-phenylacetamide scaffold in order to generate antibodies with broad immune specificity for virtually all fentanyl derivatives (FIG. 1). Furthermore, the propanoyl group in fentanyl was selected as the point of linker attachment because it would not sterically encumber the core structure (FIG. 1). Hapten synthesis was achieved via replacement of the propanoyl group in fentanyl with a glutaric acid moiety, enabling standard bioconjugate chemistry for amide coupling to an immunogenic carrier protein. Tetanus toxoid (TT) protein was chosen because of its use as a component of clinically-approved tetanus and glycoconjugate vaccines, Following conjugation of the fentanyl hapten to TT surface lysines, the resulting immunoconjugate (termed Fent-17, FIG. 1) was administered to mice. Fent-TT was formulated with adjuvants alum and CpG ODN 1826 which have proven effective in boosting IgG antibody responses to a heroin conjugate vaccine.[14a] As shown in FIG. 2, the Pent-TT vaccine induced very high anti fentanyl antibody mid-point titers by ELISA (>100,000) even after one injection, providing ample in vivo neutralization capacity for fentanyls.

To assess vaccine performance, we employed antinociception assays that are a standard method for measuring the analgesic potential of opioid drugs in rodent models;[14a, 16] opioids such as fentanyl increase pain thresholds in a dose-responsive manner, and these thresholds can be quantified by measuring animal latency to nociception induced by a hot surface. A drug vaccine will blunt the pharmacological action of the target drug via serum antibody-mediated immunoantagonism of an administered dose; therefore, a successful vaccine should shift the drug dose-response curve in antinociception assays to the 'right'. Comparison of drug $ED_{50}$ doses in vaccinated and non-vaccinated mice serves as a useful metric for drug vaccine efficacy. Previously, we have reported vaccine-induced shifts of about 5-10 fold which caused heroin-dependent rats to extinguish drug self-administration.[14b, 14b] In the current study, we observed large fentanyl ED shifts of over 30-fold. Remarkably, during the initial week 6 testing session, fentanyl dosing was incapable of overriding the protective capacity of the vaccine. One month later (week 10), anti-drug titers in vaccinated mice had decreased to a point where smaller fentanyl doses could be used to generate full dose-response curves for $ED_{50}$ determination; large vaccine-mediated shifts were observed (33-fold in the tail immersion test, FIG. 3). Strikingly, at the two largest doses that were safely administered to vaccinated mice (2.2 and 4.4 mg/kg), untreated mice experienced a 18 and 55% fatality rate respectively, thus demonstrating the ability of the vaccine to block lethal fentanyl doses.

As a testament to the vaccine's ability to neutralize other fentanyl analogues, Fent-TT immunized mice showed protection from two of the most common illegal fentanyl derivatives, 3-methylfentanyl and α-methylfentanyl aka "China White" (see FIG. 1 for structures). The α-Me analogue was equipotent with the parent compound, and the vaccine was able to shift the α-Me $ED_{50}$ by about 8-fold (FIG. 3). On the other hand, the 3-Me analogue was extraordinarily potent (about 10-fold greater than fentanyl), yet the vaccine still produced a 4-fold $ED_{50}$ shift (FIG. 3). Overall, our behavioral results indicate that the Fent-TT vaccine provided ample attenuation of large fentanyl doses in vivo while demonstrating a therapeutically useful level of cross-reactivity to fentanyl analogues. Clinically, these results implicate Pent-TT as an effective addiction therapy for curbing fentanyl abuse and overdose-induced lethality.

From a pharmacokinetic standpoint, we investigated the effect of the Pent-TT vaccine on the biodistribution of a fentanyl dose. Following administration of a fentanyl dose, we sacrificed both control and vaccinated mice at roughly the $t_{max}$ (time at peak drug plasma concentrations) and measured fentanyl concentrations in both brain and blood samples by LCMS. Our results clearly show how serum antibodies in vaccinated mice act as a depot to bind 45 times the amount of fentanyl relative to serum proteins in control mice. This translated to a significant reduction in fentanyl brain concentrations of vaccinated mice, lending to a pharmacological explanation of how the vaccine attenuates fentanyl psychoactivity.

Behavioral and pharmacokinetic results were corroborated with thorough biochemical analysis of antiserum derived from Fent-TT vaccinated mice. To achieve this, we employed surface plasmon resonance (SPR) spectroscopy, a highly sensitive technique for investigating protein-protein or protein-small molecule binding interactions.[17] In a new application of SPR, we measured binding affinities of polyclonal antibodies in vaccinated mouse serum for various fentanyl analogues. Diluted mouse serum was preincubated with a series of concentrations of selected fentanyl derivatives and then injected into a Biacore 3000 containing a Fent-BSA coated chip. Essentially, this method is a more sophisticated version of competitive ELISA in which serially-diluted free drug competes with an immobilized drug hapten for antibody binding.[18] Our results from the SPR competition experiment (FIG. 5a) indicated that antibodies from Fent-TT immunized mice have high affinity for fentanyl derivatives, generating binding curves with low nanomolar $IC_{50}$ values and limits of detection in the pM range (see FIG. 5a and raw sensorgrams). Relative affinities between analogues with different $R_1$ alkyl groups were very similar, likely due to the fact that the $R_1$ position was used as a linker attachment point. As expected, methylation at other positions resulted in lower affinity but still $IC_{50}$ values were <100 nM. Furthermore, the SPR $IC_{50}$s mirrored the results in behavioral assays, and in both cases followed a trend of Fent>α-Me>cis-3-Me. Since the Fent-TT vaccine gave broad specificity to fentanyl class drugs, two clinically used opioids methadone (MeD) and oxycodone (Oxy) were tested to ensure minimal cross reactivity. Indeed, affinities for these opioids were >7,500 times lower compared to fentanyl (FIG. 5a), demonstrating that they could still be used in Fent-TT vaccinated subjects.

Figure 5B:
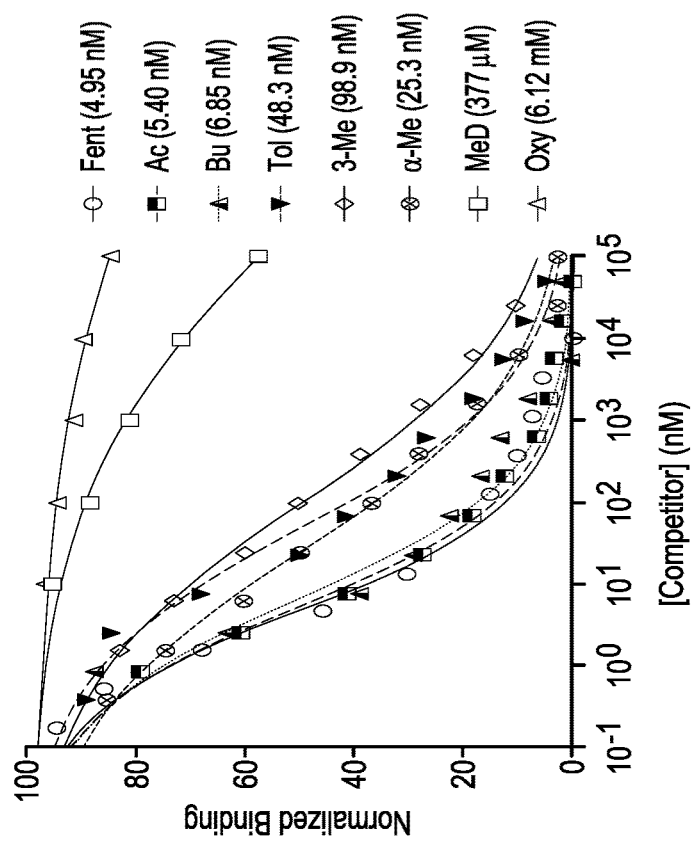
FIG. 5. Antiserum opioid binding curves and SPR sensorgrams. a) Diluted mouse serum from week 6 was incubated with serial dilutions of the listed opioids and injected into a Biacore 3000 containing a Pent-BSA loaded sensor chip, Signal produced by antibody binding to the SPR chip without drug present was used as a reference for 100% binding. Fentanyls used were racemic and 3-Me was cis. See FIG. 1 for structures, b) Overlaid plots of sensorgrams obtained for the interaction between fentanyl (1000, 500, 250, 125, 62.5, 31.25, 15.63, 7.81, 3.9, 1.95 and 0 nM) and immobilized anti-fentanyl antibodies at 26° C. on a BiOptix 404pi, Original experimental sensorgrams are shown in black and fitted curves are traced in white.
Figure 5A:
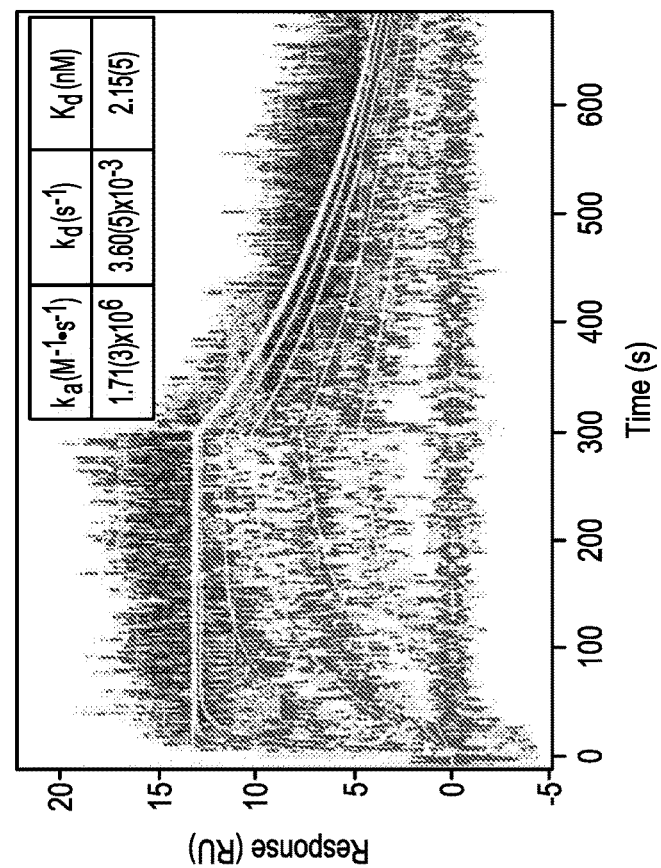

Further validation of the SPR method was pursued to confirm that the generated $IC_{50}$ values were representative of actual $K_D$; hapten affinity does not always reflect free drug affinity. To address this problem, we affinity purified anti-fentanyl antibodies and loaded them onto an SPR chip for direct measurement of free fentanyl binding kinetics. As shown in FIG. 5b sensorgrams, the fentanyl $K_b$ of purified antibodies (2 nM), is in close agreement with the $IC_{50}$ value determined by the competition method (5 nM). Thus, we have demonstrated the SPR competition method as an accurate way to measure drug affinities of polyclonal serum antibodies. A crucial aspect of immunopharmacotherapy is proper characterization of anti-drug antibodies, and the SPR method could help to facilitate this facet of drug vaccine development. Additionally, the method could be used to screen biological samples e.g. blood or urine for the presence of a wide variety of fentanyl derivatives, especially since the limit of detection for many fentanyl analogues is <1 nM (FIG. 5a).

The current study has yielded a potential therapeutic that could assist in combatting the rise of opioid abuse. An effective fentanyl conjugate vaccine was developed that easily ablates small doses needed to achieve a normal drug-induced 'high' but also attenuates large, potentially lethal doses of fentanyl class drugs. Furthermore, the success of this vaccine helps to advance immunopharmacotherapy from an academic novelty towards a practical therapy, and influences the creation of vaccines against other destructive designer drugs such as 'bath salts'.[4, 19]

DOCUMENTS CITED

[1] P. A. Janssen, *British Journal of Anaesthesia* 1962, 34, 260-268,

[2] J. M. White, R, J. Irvine, *Addiction* 1999, 94, 961-972.

[3] G. L Henderson, *J Forensic Sci* 1991, 36, 422-433.

[4] F. I. Carroll, A. H. Lewin, S. W. Mascarene, H. H. Seltzman, P. A. Reddy, *Ann Ny Aced Sol* 2012, 1248, 18-38.

[5] W. F. Van Bever, C. J. Niemegeers, P. A. Janssen, *J Med Chem* 1974, 17, 1047-1051.

[6] NIDA, *Emerging Trends* 2015,

[7] M. Martin, J. Hecker, R. Clark, J. Frye, D. Jehie, E J. Lucid, F. Harchelroad, *Ann Emerg Med* 1991, 20, 158-164.

[8] J. M. Stogner, *Ann Emerg Med* 2014, 64, 637-639.

[9] C, Centers for Disease, Prevention, *MMWR Morb Mortal Wkly Rep* 2013, 62, 703-704.

[10] J. Mounteney, L Giraudon, G. Denissov, P. Griffiths, *Int J Drug Policy* 2015, 26, 626-631,

[11] a) B. A. Martell, E. Mitchell, J. Poling, K. Gonsai, T. Kosten, *Biol Psych* 2005, 58, 158-164; b) M. R. A. Carrera, J. A. Ashley, B. Zhou, P. Wirsching, G, F. Koob, K. D. Janda, *PNAS* 2000, 97, 6202-6206.

[12] a) M. Pravetoni, D. E Keyler, R. P. Pidaparthi, F. I. Carroll, S. P. Runyon, M. P. Murtaugh, C. A, Earley, P, R. Pentel, *Biochemical Pharmacology* 2012, 83, 543-550; b) J. W, Lockner, J. M. Lively, K. C. Collins, J, C. M. Vendruscolo, M. R. Azar, K. D, Janda, *J Med Chem* 2015, 58, 1005-1011.

[13] a) A. Y. Moreno, A. V. Mayorov, K. D. Janda, *JACS* 2011, 133, 6587-6595; b) D. Ruedi-Bettschen, S. L. Wood, M. G. Gunnell, C. M. West, R. R. Pidaparthi, F. I. Carroll, B. E. Blough, S M. Owens, *Vaccine* 2013, 31, 45964602,

[14] a) R. T. Bremer, J. E, Schlosburg, J. M. Lively, K. D. Janda, *Mol Phar* 2014, 11, 1075-1080; b) J. E. Schlosburg, L. F. Vendruscolo, P. T, Bremer, J. W. Lockner, C. L, Wade, A, A. Nunes, G. N. Stowe, S. Edwards, K. D. Janda, G. F. Koob, *PNAS* 2013, 110, 9036-9041; c) K. D. Janda, J, B. Treweek, *Nature Reviews immunology* 2012, 12, 67-72; d) R. Jalah, O. B. Torres, A. V. Mayorov, F. Y. Li, J. F. G. Antoline, A. E. Jacobson, K. C. Rice, J. R. Deschamps, Z. Beck, C. R. Alving, G. R, Matyas, *Bioconjugate Chemistry* 2015, 26, 1041-1053,

[15] a) G. N. Stowe, L. F. Vendruscolo, S. Edwards, J. E. Schiosburg, K. K. Misra, G. Schulteis, A. V. Mayorov, J. S. Zakhari, G. F. Koob, K. D. Janda, *J Med Chem* 2011, 54, 5195-5204; b) P. T. Bremer, K. D. Janda, *J Med Chem* 2012, 55, 10778-10780.

[16] A. W. Bannon, A. B. Malmberg, *Curr Protoc Neurosci* 2007, Chapter 8, Unit 8 9.

[17] a) G. Kienkar, B. Liedberg, *Anal Bioanal Chain* 2008, 391, 1679-1688; b) G. Sakai, K. Ogata, T Uda, N. Miura, N. Yamazoe, *Sensor Actuat B-Chem* 1998, 49, 5-12.

[18] a) W. Runagyuttikam, M. Y. Law, D. E. Rollins, a E. Moody, *Journal of Analytical Toxicology* 1990, 14, 160-164; b) G. S. Makowski, J. J. Richter, R. E. Moore, R. Eisma, D. Ostheimer, M. Onoroski, A. H. B. Wu, *Ann Clin Lab Sci* 1995, 25, 169-178.

[19] C. L. German, A. E. Fleckenstein, a R. Hanson, *Life sciences* 2014, 97: 2-8.

EXAMPLES

Chemistry

Nuclear magnetic resonance ($^1$H NMR (400 MHz), $^{13}$C NMR (100 MHz)) spectra were determined on a Braker 400 instrument unless otherwise noted. Chemical shifts for $^1$H NMR are reported in parts per million (ppm) relative to chloroform (7.26 ppm) and coupling constants are in hertz (Hz). The following abbreviations are used for spin multiplicity: s=singlet, d=doublet, t=triplet, o=quartet, m=multiplet, br=broad. Chemical shifts for $^{13}$C NMR were reported in ppm relative to the center line of a triplet at 77.0 ppm for chloroform. Electrospray Ionization (ESI) mass were obtained on a ThermoFinnigan LTQ Ion Trap. Matrix-assisted Laser Desorption/Ionization (MALDI) mass spectra were obtained on an Applied Biosystems Voyager DE. Analytical thin layer chromatography (TLC) was performed on Merck precoated analytical plates, 0.25 mm thick, silica gel 60 $F_{254}$. Preparative TLC (PTLC) separations were performed on Merck analytical plates (0.50 mm thick) precoated with silica gel 60 $F_{254}$. Flash chromatography separations were performed on Aldrich silica gel (catalog #717185, 60 Å pore size, 40-63 μm particle size, 230-400 mesh) unless otherwise noted.

Animal Experiments 6-8 week old male Swiss Webster mice (n=6/group) were obtained from Taconic Farms (Germantown, N.Y.). Mice were group-housed in an AAALAC-accredited vivarium containing temperature- and humidity-controlled rooms, with mice kept on a reverse light cycle (lights on: 9 PM-9 AM). All experiments were performed during the dark phase, generally between 1 PM-4 PM. General health was monitored by both the scientists and veterinary staff of Scripps Research Institute, and all studies were performed in compliance with the Scripps Institutional Animal Care and Use Committee, and were in concordance with the National Institutes of Health Guide for the Care and Use of Laboratory Animals. Blood serum samples for titer quantification were performed using tail-tip amputation (<1 cm) in order to collect between 100-150 μL whole blood, and samples then centrifuged at 7500 rpm for 8 min to separate serum.

Fentanyl Hapten Synthesis

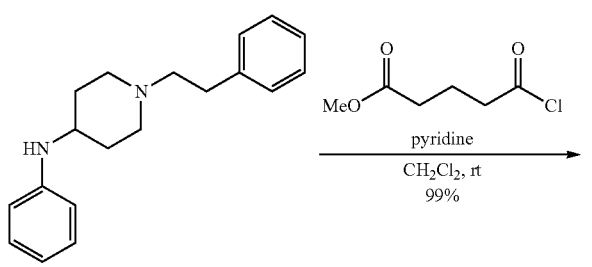

1

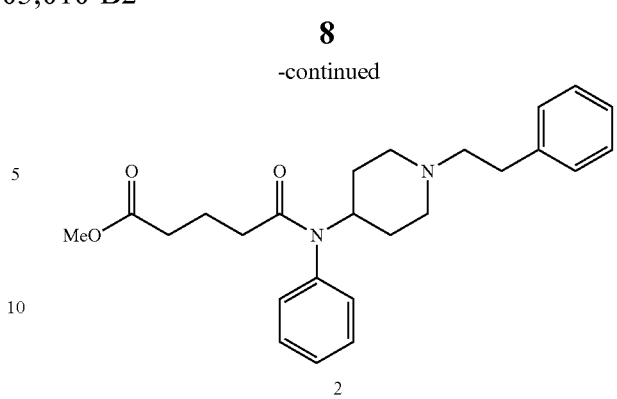

2

To a solution of 1[1] (200 mg, 714 μmol) in $CH_2Cl_2$ (7.0 mL) were added pyridine (115 μL, 1.42 mmol) and glutaric acid monomethyl ester chloride (110 μL, 780 μmol) at 0° C. After stirring at 0° C. for 5 min, the reaction mixture was allowed to warm to rt. After stirring at rt for 1.5 h, the reaction mixture was quenched with saturated aqueous $NeHCO_3$, and extracted with EtOAc. The aqueous layer was extracted with EtOAc three times. The combined organic extracts were dried over $Na_2SO_4$, filtered, and evaporated in vacuo. The residual oil was purified by flush column chromatography ($SiO_2$; n-hexane:EtOAc=1:1 to 1:2 to 0:1) to afford 2 (288 mg, 98.7%) as a pale yellow solid.

$^1$H-NMR (400 MHz, $CDCl_3$) δ 7.41-7.35 (m, 3H), 7.27-7.23 (m, 2H), 7.19-7.13 (m, 3H), 7.08-7.05 (m, 2H), 4.67 (tt, J=12.0, 4.0 Hz, 1H), 3.59 (s, 3H), 2.99 (br d, J=12.8 Hz, 2H), 2.72 (dd, J=8.4, 8.0 Hz, 1H), 2.72 (d, J=6.4 Hz, 1H), 2.53 (dd, J=8.4, 7.2 Hz, 1H), 2.26 (t, J=7.2 Hz, 2H), 2.15 (td, J=12.4, 2.4 Hz, 2H), 1.98-1.93 (m, 2H), 1.87 (qd, J=7.6, 1.6 Hz, 3H), 1.85-1.77 (m, 2H), 1.42 (qd, J=12.4, 3.6 Hz, 2H); $^{13}$C-NMR (100 MHz, $CDCl_3$) δ 173.5, 171.7, 139.7, 138.4, 130.2 (2C), 129.3 (2C), 128.5 (2C), 128.3, 128.3 (2C), 126.0, 59.9, 52.6 (2C), 51.9, 51.3, 33.9, 33.2, 33.1, 29.9 (2C), 20.5; HRMS (ESI+) 409.2487 (calcd for $C_{25}H_{33}N_2O_3$ 409.2491).

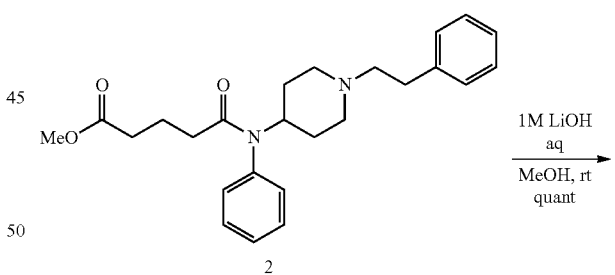

2

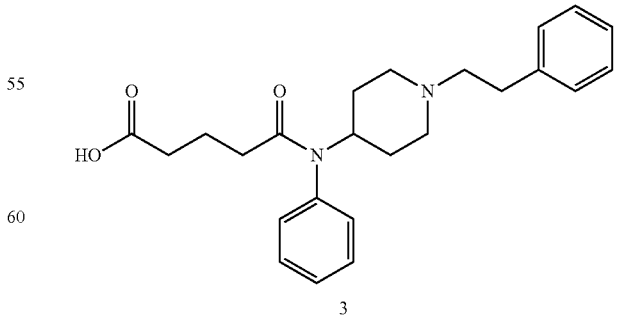

3

To a solution of 2 (49.9 mg, 122 μmol) in MeOH (1.0 mL) was added 1.0 M aqueous LiOH (250 μL) at rt. After stirring at rt for 4 h, the reaction mixture was washed with hexane. The aqueous layer was acidified with 2.0 M aqueous HCl, and extracted with EtOAc three times. The combined organic extracts were dried over Na$_2$SO$_4$, filtered, and evaporated in vacuo. The residual white solid 3[2] (52.0 mg, quant) was used for the next step without further purification. The spectroscopic data for 3 were collected after purification by PTLC (SiO$_2$; CH$_2$Cl$_2$:MeOH=9:1).

$^1$H-NMR (400 MHz, CDCl$_3$) δ 7.41-7.35 (m, 3H), 7.29-7.24 (m, 2H), 7.22-7.18 (m, 1H), 7.17-7.15 (m, 2H), 7.06-7.04 (m, 2H), 4.83 (br s, 1H), 4.69 (tt, J=12.0, 4.0 Hz, 1H), 3.35 (br d, J=11.6 Hz, 2H), 2.96-2.85 (m, 4H), 2.56 (br t, J=10.8 Hz, 2H), 2.16 (t, J=7.2 Hz, 2H), 1.98 (t, J=7.2 Hz, 2H), 1.87 (br d, J=12.4 Hz, 2H), 1.83-1.74 (m, 2H), 1.80 (t, J=6.8 Hz, 2H); $^{13}$C-NMR (100 MHz, CDCl$_3$) δ 176.9, 172.3, 139.0, 138.4, 130.0 (2C), 129.5 (2C), 128.6 (2C), 128.6, 128.5 (2C), 126.3, 59.2, 52.3 (2C), 51.7, 34.3, 34.1, 32.3, 29.2 (2C), 20.9; HRMS (ESI+) 395.2327 (calcd for C$_{24}$H$_{31}$N$_2$O$_3$ 395.2335).

Fentanyl Hapten Conjugation to Bovine Serum Albumin (BSA) and Tetanus Toxoid (TT)

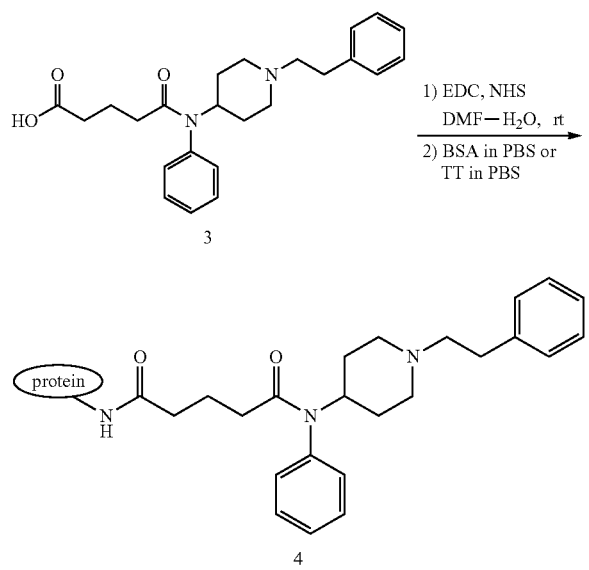

To a solution of 3 (2.7 mg, 6.8 μmol) in DMF (144 μL) and H$_2$O (16 μL) were added NHS (N-hydroxysuccinimide) (4.8 mg, 40.4 μmol) and EDC (N-(3-dimethylaminopropyl)-N'-ethylcarbodiimide) (7.8 mg, 40.8 μmol) at rt. After stirring at rt for 1.5 h, additional EDC (4.2 mg, 21.9 μmol) was added. After additional stirring at rt for 2 h, the reaction mixture was divided into two portions.

One portion (80 μL) was added into a solution of BSA (Thermo Scientific) in PBS buffer (pH 7.4) (660 μL, 1.50 mg/mL) at rt, and the other portion (80 μL) was added into a solution of TT (Staters Serum Institut) in PBS buffer (pH 7.4) (650 μL, 1.53 mg/mL) at rt. After stirring at rt for 15 h, each of the reaction mixture was dialyzed against PBS buffer (pH 7.4) at rt using a Slide-A-Lyzer 10 K MWCO dialysis device. The buffer was exchanged every 2 h for 6 h, and then dialysis was continued for 12 h at 4° C. The conjugate concentrations were quantified by BCA assay and stored at 4° C.

Preparation of Fentanyl Hapten Coated Dynabeads® M-270 Amine

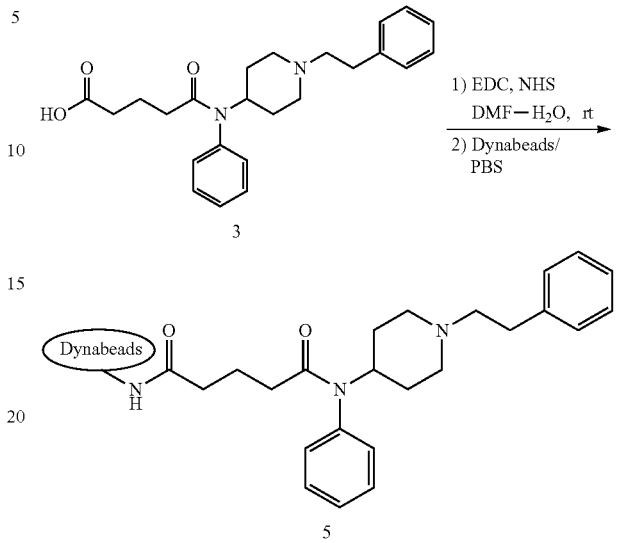

To a solution of 3 (3.0 mg, 7.8 μmol) in DMF (225 μL) and H$_2$O (25 μL) were added NHS (9.0 mg, 75.8 μmol) and EDC (14.6 mg, 76.1 μmol) at rt. After stirring at rt for 12 h, a 50 μL aliquot of the reaction mixture was added into 1.0 mL of DYNABEADS® M-270 Amine (washed 4 times with PBS buffer (pH 7.4) prior to use) in PBS buffer at rt. After stirring at rt for 1.5 h, the beads were washed with PBS buffer (pH 7.4) for two times and stored at 4° C.

MALDI-TOF Analysis

In order to quantify copy number (hapten density) for each fentanyl hapten-BSA and TT conjugates prepared in this study, samples were submitted for MALDI-TOF analysis and compared MW of fentanyl hapten-BSA and TT conjugates with MW of unmodified BSA and TT, respectively, as per the formula:

copy number=(MW$_{fentanyl\ hapten-protein}$−MW$_{protein}$)/(MW$_{fentanyl\ hapten}$−MM$_{water}$)

MW$_{fentanyl\ hapten}$=395 Da, MW$_{water}$=18 Da
MM$_{fentanyl\ hapten-BSA}$=80,939 Da, MW$_{BSA}$=66,500 Da
MW$_{fentanyl\ hapten-TT}$=168,757 Da, MW$_{TT}$=153,500 Da
copy number$_{fentanyl\ hapten-BSA}$=38
copy number$_{fentanyl\ hapten-TT}$=40

ELISA Procedure

Pipetting and washing steps were performed on a Biomek 3000 liquid handling robot. PBS was used throughout the assay at pH 7.4 and was prepared from a 10× powder packet from Fisher Scientific. First, half-area high-binding 96 well microtiter plates (Costar 3690) were coated with 25 μg of Fent-BSA per well overnight at 37° C., allowing the liquid to evaporate. Following blocking with skim milk for 1 h at rt, vaccinated mouse serum was serially diluted 1:1 in 2% BSA solution across the 12 columns starting at 1:5000. After a 2 h incubation at rt, the plates were washed 5× and donkey anti-mouse IgG HRP secondary (Jackson ImmunoResearch) at a 1:10,000 dilution in 2% BSA was added and incubated for 1 h at rt. 5× washing was performed and TMB substrate (Thermo Pierce) was added, followed by 2M H$_2$O. 5 min after TMB addition. Plates were allowed to incubate 20 min before their absorbances were read at 450 nm. In GraphPad PRISM, absorbance values were normalized to the highest absorbance value per sample, and a curve was fit using the log(inhibitor) vs. normalized response variable slope equation to determine the 50% titer and standard errors. Non-vaccinate mice did not contain any detectable anti-fentanyl titers.

Animal Procedure for Blood/Brain Biodistribution Study

Mice (n=6 vaccinated and n=6 control) were injected with subcutaneously with 0.2 mg/kg fentanyl, an established fully analgesic dose in nave mice, in a 10 mL/kg volume of physiological sterile saline. 15 min following injection, mice were fully anesthetized using nose cones constructed from 50 mL Falcon® conical centrifuge tubes (Corning, N.Y.) containing gauze pads soaked in isoflurane. Mice were then opened along the midline just below the sternum and the diaphragm peeled back to expose the heart. Cardiac puncture yielded roughly 1.5 mL of whole blood. Immediately following cardiac puncture, mice were rapidly decapitated using large surgical scissors and brain extracted with rongeurs. The brain was then weighed (typically between 4.0-6.0 g) and lightly washed in a 1.0 mL solution of ice-cold standard PBS to remove excess external blood; however, mice were not perfused to fully remove all blood that may have been contained within ventricles and internally within the brain matter. Brains were then added to 1.0 mL fresh ice-cold PBS in 5.0 mL conical sample tubes and homogenized using a Tissue Tearer (Biospec; Bartlesville, Okla.). Samples of both brain and serum were then frozen until sample prep for LCMS analysis.

Sample Preparation and Extraction for LC-MS Analysis of Fentanyl in Blood and Brain[3]

To an aliquot of sample (400 μL, blood or homogenized brain) was added fentanyl-$d_5$ (20 μL, 50 ng/mL) in MeOH as an internal standard, and then the mixture was vortex mixed and allowed to equilibrate. After 30 min for equilibration, $H_2O$ (400 μL) was added to the mixture, Basification was obtained by addition of 0.1 M aqueous $K_2CO_3$ solution (400 μL) followed by agitation using a vortex mixer. Extraction was conducted with mixture of n-hexane and EtOAc (7:3) (2.8 mL). After vortex mixing for 2 min and centrifugation at 3000 rpm for 5 min, the organic layer was evaporated using GENEVAC®. An 8 μL aliquot was injected into LC-MS system equipped with an Agilent Poroshell 120 SB-C8 column using 5 mM $NH_4OAr$ pH 4/acetonitrile mobile phase. A blank was injected before every sample. Dautereted and non-deuterated masses were extracted in MassHunter and resulting peaks were integrated. Using the ratio of non-deuterated to deuterated integration values, fentanyl concentrations were determined via a six point standard curve (see below). Standards for the calibration curve were prepared in the same manner as tissue samples except with samples of known non-deuterated fentanyl concentration&

Vaccine Formulation and Administration

On a per mouse basis, 50 μg Fent-TT+50 μg CpG ODN 1826 (Eurafins) in 75 μL pH 7.4 PBS was combined with 75 μL (0.75 mg) Alhydrogel (Invivogen) and mixed for 30 min. The suspension (150 μL per mouse) was injected intraperitoneally to 6 mice at weeks 0, 2, 4, Mice were bled at weeks 2, 4, 6, 10 and 12.

Opioid Antinociceptive Potency Testing

At least 2 days following a bleed, mice were tested for cumulative fentanyl response in primarily supraspinal (hot plate) and spinal (tail immersion) behavioral tests as previously described.[4] The hot plate test was measured by placing the mouse in an acrylic cylinder (14 cm diameter*22 cm) on a 54° C. surface and timing latency to perform one of the following nociceptive responses: licking of hindpaw, shaking/withdrawal of hindpaw, or jumping, Typical baseline latency was between 8.15 s and a 35 s cutoff was imposed to prevent tissue damage; after response mice were removed from the plate. The tail immersion test was administered by lightly restraining mice in a small pouch constructed from absorbent laboratory underpads and dipping 1 cm of the tip of the tail into a heated water bath, with the time to withdrawal timed.

Typical baseline response was 1-2 s and a cutoff of 10 s was used to prevent tissue damage. Since tail immersion is a more reflexive behavior, testing order was always hot plate first followed by tail immersion. Immediately following completion of both antinociceptive assays, fentanyl (5.0 mL/kg in normal saline) was immediately injected subcutaneously. Testing was repeated roughly 10 min following each injection, and this cycle of testing and injections was repeated with increasing cumulative fentanyl dosing until full antinociception (i.e. cutoff times surpassed) was observed in both assays, Upon completion of all testing, mice were administered a cocktail of 1.0 mg/kg naloxone and naltrexone in saline to prevent subsequent consequences of potential overdose.

Lethality Study

Male Swiss Webster mice (N=11) were injected intraperitoneally with 2.2 mg/kg fentanyl HCl in pH 7.4 PBS after which 2/11 died of overdose. A second 2.2 mg/kg fentanyl HCl dose was administered 15 min later to the remaining 9 mice after which four more (6/11) died of overdose. The same experiment (N=12) was performed subcutaneously with cumulative dosing of 0.4, 0,8, 1.6, 2.4 and 4.4 mg/kg over 1 h inducing overdose deaths in 2/12 of the mice.

Statistics

Statistical analysis was performed in GraphPad Prism 6 (La Jolla, Calif.). All values are reported as means±SEM, Antinociceptive data was transformed from time to % maximum possible effect (% MPE), which is calculated as: % MPE=(test−baseline)/(cutoff−baseline)*100. This data was then fit using a log(agonist) vs. normalized response non-linear regression. $ED_{50}$ values and 95% confidence intervals of the ED were calculated for each pain test and individual treatment group to determine potency ratios. An unpaired t test was used for verification of statistically significant differences (α<0.001) between control and vaccinated groups for blood/brain fentanyl concentrations and fentanyl $C_{50}$ shifts.

Determination of Binding $IC_{50}$s for Mouse anti-Fentanyl Immunoglobulins (16s)

The binding $IC_{50}$ for mouse IGs and free fentanyl was determined by competitive binding assay via surface plasmon resonance using a Biacore 3000 instrument (GE Healthcare) equipped with a research-grade CM3 sensor chip. The ligand, fentanyl-BSA conjugate, was immobilized using NHS, EDC coupling reaction. The surface of all two flow cells (flow cells 1 and 2) were activated for 7 min with a 1:1 mixture of 0.1 M NHS and 0.1 M EDC at a flow rate of 5 μL/min. The ligand resuspended in 10 mM sodium acetate (pH 4.0) was immobilized at a density of 2,000 RU on flow cell 2; whereas flow cell 2 was immobilized with BSA at the same density to serve as a reference surface. All the surfaces were blocked with a 7 min injection of 1.0 M ethanolamine-HCl (pH 8.5). The mouse IGs were diluted in running buffer (HBS-EP+ buffer) and titrated on both coated flow cells, so as to give a response of ~60 RU with 3 min of injection and 2.6 min dissociation at a flow rate of 30 μL/min. The mouse ICs prepared in HBS-EP+ buffer at determined concentration was incubated with a series concentration of compounds for 1 h at room temperature before conducting the competitive binding assay. The compounds and their concentration series are as follows: a) fentanyl, ranging from 10 μM to 169 pM with a three-fold dilution series; b) acetylfentanyl, butyrylfentanyl, and p-tolylfentanyl, ranging from 50 mM to 850 pM with three-fold dilution; c) cis-3-methylfentanyl, and α-methylfentanyl (China White), ranging from 100 mM to 95 pM, four-fold dilution series; d) methadone and oxycodone, ranging from 100 mM to 10 nM, ten-fold dilution series. Note, all fentanyls were racemic. To collect binding data, the analyte, the mouse IGs and compound mixture, was injected over the two flow cells at a flow rate of 30 μL/min at 25° C. for 3 min and was dissociated in buffer for 2.5 min before regeneration. The chip surface was regenerated by injection of 10 mM Gly-HCl (pH1.5) for 30 seconds before the next round of assay. The response at the end of dissociation phase for each cycle of binding analysis was used to calculate the $IC_{50}$ value for each compound by GrephPad Prism 6 software. The binding curves are illustrated in FIG. 5a.

Determination of Binding Kinetics for Purified Mouse Anti-Fentanyl Immunoglobulins (IGs)

The binding kinetics between mouse IGs (purified directly from week 6 bleed using magnetic fentanyl-coupled Dynabeads) and free fentanyl were determined by surface plasmon resonance using a BiOptix 404pi instrument (BiOptix Diagnostics, Inc., Boulder, Co.) equipped with a CMD200m sensor chip. The ligand, mouse anti-fentanyl IgGs (~150 kDa), were immobilized using NHS, EDC coupling reaction. The surface of all two flow cells (flow cells 2 and 3, assay set at 2*2 injection mode) were activated for 7 min with a 1:1 mixture of 0.1 M NHS and 0.1 M EDC at a flow rate of 5 μL/min. The ligand resuspended in 10 mM sodium acetate (pH 4.5) was immobilized at a density of 12,000 RU on flow cell 3: whereas flow cell 2 was immobilized with a non-related antibody at the same density to serve as a reference surface. All the surfaces were blocked with a 7 min injection of 1.0 M ethanolamine-HCl (pH 8.5). To collect kinetic data, the analyte, fentanyl (336.48 Da) prepared in HBS-EP+buffer (10 mM HEPES, 150 mM NaCl, 0.05% P20 (pH 7.4)), was injected over the two flow cells at concentration range from 1,000-1.95 nM (two-fold dilution series) at a flow rate of 50 μL/min at a temperature of 25° C. The complex was allowed to associate and dissociate for 300 and 900 s, respectively. Duplicate injections (in random order) of each analyte sample and blank buffer injections were flowed over the two surfaces, Data were collected, double referenced, and were fit to a 1:1 interaction model using the global data analysis by Scrubber 2. The kinetic data are shown in FIG. 5b.

DOCUMENTS CITED IN EXAMPLES

[1] C. A. Valdez, R. N. Leif, B. P. Mayer, Plos One 2014, 9.
[2] R. Vardanyan, V. K. Kumirov, G. S. Nichol, P. Davis, E. Liktor-Busa, D. Rankin, E. Varga, T. Vandersh, F. Porreca, J. Lai, V. J. Hruby, Bioorg Med Chem 2011, 19, 6135-6142.
[3] V. Coopman, J. Cordonnier, K. Pien, D. Van Varenbergh, Forensic Sci Int 2007, 169, 223-227
[4] P. T. Bremer, J. E. Schlosburg, J. M. Lively, K. D, Janda, Mol Pharm 2014, 11, 1075-1080.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims,

7. A hapten conjugate having the formula:
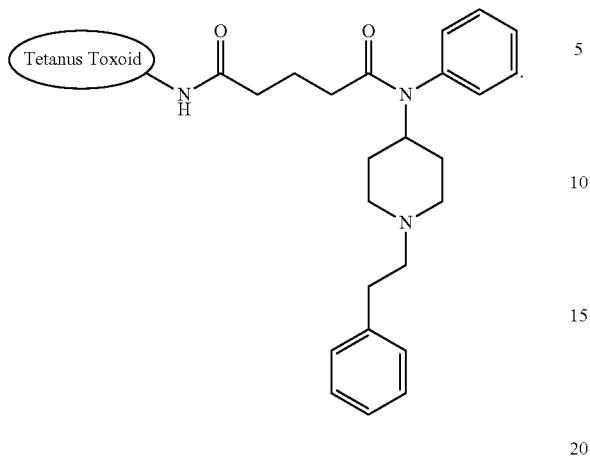

What is claimed is:

1. A hapten conjugate of formula (I):

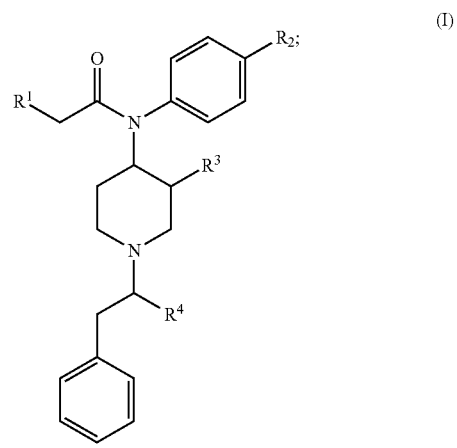

wherein $R^1$ is —$CH_2CH_2C(=O)X$,

X is a tetanus toxoid; wherein the tetanus toxoid forms an amide bond with the —C(=O)— group of —$CH_2CH_2C(=O)$— in $R^1$, $R^2$ is —H or a ($C_1$-$C_4$)alkyl group, $R^3$ is —H or a ($C_1$-$C_4$)alkyl group, and $R^4$ is —H or a ($C_1$-$C_4$)alkyl group.

2. A vaccine comprising the hapten conjugate of claim 1 and an adjuvant.

3. The vaccine of claim 2, wherein the vaccine is effective in eliciting an IgG antibody response for a fentanyl class drug.

4. A method of effectively minimizing a concentration of a fentanyl class drug in a patient in need thereof, comprising administering to the patient an effective dose of the vaccine of claim 2.

5. The method of claim 4, wherein administering the effective dose of the vaccine imparts protection to the patient from an otherwise lethal dose of a fentanyl class drug.

6. The method of claim 4, wherein administering the effective does of the vaccine to the patient reduces the addiction liability and overdose potential of the fentanyl class drug.